(12) United States Patent
Williams

(10) Patent No.: US 9,757,129 B2
(45) Date of Patent: Sep. 12, 2017

(54) COUPLING MEMBER CONFIGURED FOR USE WITH SURGICAL DEVICES

(71) Applicant: Covidien LP, Mansfield, MA (US)

(72) Inventor: Justin Williams, Naugatuck, CT (US)

(73) Assignee: Covidien LP, Mansfield, MA (US)

( * ) Notice: Subject to any disclaimer, the term of this patent is extended or adjusted under 35 U.S.C. 154(b) by 936 days.

(21) Appl. No.: 13/936,289

(22) Filed: Jul. 8, 2013

(65) Prior Publication Data

US 2015/0012014 A1 Jan. 8, 2015

(51) Int. Cl.
*A61B 17/10* (2006.01)
*A61B 17/072* (2006.01)
(Continued)

(52) U.S. Cl.
CPC ...... *A61B 17/07207* (2013.01); *A61B 2017/0046* (2013.01); *A61B 2017/00473* (2013.01); *F16B 7/042* (2013.01); *F16D 1/108* (2013.01)

(58) Field of Classification Search
CPC ............ A61B 1/00121; A61B 1/00112; A61B 2562/225; A61B 17/07207; A61B 2018/00172; A61B 17/0783; A61B 2017/07214; A61B 2017/07271; A61B 17/068; B25F 3/00; Y10T 403/32467; Y10T 403/32475; Y10T 403/32483;
(Continued)

(56) References Cited

U.S. PATENT DOCUMENTS 2,291,593 A * 7/1942 Hubbard .................. B25G 1/04
294/174
2,319,992 A * 5/1943 Hubbard .................. B25G 1/04
174/5 R
(Continued)

FOREIGN PATENT DOCUMENTS

EP 0634144 1/1995
EP 1690502 8/2006
(Continued)

OTHER PUBLICATIONS

European Search Report dated Nov. 12, 2014 issued in European Appln. No. 14175923.
(Continued)

*Primary Examiner* — Gloria R Weeks
*Assistant Examiner* — Lucas Palmer

(57) ABSTRACT

A surgical apparatus is provided. The surgical apparatus includes a surgical actuating device including a shaft having supporting a first coupling member. The first coupling member includes one or more pairs of apertures. The reload includes a second coupling member including a locking assembly. The second coupling member includes a pair of spring pins positionable within the pair of apertures. The spring pins being movable from an inward position to a radial outward position. The locking assembly includes a lock plate that is moveable from a first position located between the spring pins to a second position spaced from the spring pins. In the radial outward position, the spring pins are received within the apertures of the first coupling mem-
(Continued)

ber to secure the reload to the surgical actuating member and when the lock plate is in the first position, the reload cannot be separated from the surgical actuating device.

10 Claims, 7 Drawing Sheets

(51) Int. Cl.
    *A61B 17/00*     (2006.01)
    *F16B 7/04*     (2006.01)
    *F16D 1/108*     (2006.01)

(58) Field of Classification Search
    CPC ..... Y10T 403/32508; Y10T 403/32516; Y10T 403/32524
    USPC .......................... 403/109.3; 227/175.1, 175.4
    See application file for complete search history.

(56) References Cited

U.S. PATENT DOCUMENTS

| | | | |
|---|---|---|---|
| 2,719,688 | A * | 10/1955 | Seifert ................ A47F 7/06 248/188.5 |
| 2,777,340 | A | 1/1957 | Hettwer et al. |
| 2,807,473 | A | 9/1957 | Kiehne |
| 2,957,353 | A | 10/1960 | Babacz |
| 3,111,328 | A | 11/1963 | Di Rito et al. |
| 3,695,058 | A | 10/1972 | Keith, Jr. |
| 3,734,515 | A | 5/1973 | Dudek |
| 3,759,336 | A | 9/1973 | Marcovitz et al. |
| 4,021,920 | A | 5/1977 | Kirschner et al. |
| 4,162,399 | A | 7/1979 | Hudson |
| 4,247,216 | A * | 1/1981 | Pansini .................. B25G 3/18 15/1.7 |
| 4,606,343 | A | 8/1986 | Conta et al. |
| 4,692,073 | A | 9/1987 | Martindell |
| 4,699,550 | A | 10/1987 | Baker |
| 4,705,038 | A | 11/1987 | Sjostrom et al. |
| 4,874,181 | A | 10/1989 | Hsu |
| 5,083,883 | A | 1/1992 | Ueda et al. |
| 5,129,118 | A | 7/1992 | Walmesley |
| 5,129,570 | A | 7/1992 | Schulze et al. |
| 5,152,744 | A | 10/1992 | Krause et al. |
| 5,222,956 | A | 6/1993 | Waldron |
| 5,312,023 | A | 5/1994 | Green et al. |
| 5,326,013 | A | 7/1994 | Green et al. |
| 5,330,480 | A | 7/1994 | Meloul et al. |
| 5,347,988 | A | 9/1994 | Hori |
| 5,350,355 | A | 9/1994 | Sklar |
| 5,380,333 | A | 1/1995 | Meloul et al. |
| 5,383,874 | A | 1/1995 | Jackson et al. |
| 5,383,880 | A | 1/1995 | Hooven |
| 5,389,098 | A | 2/1995 | Tsuruta et al. |
| 5,395,033 | A | 3/1995 | Byrne et al. |
| 5,400,267 | A | 3/1995 | Denen et al. |
| 5,413,267 | A | 5/1995 | Solyntjes et al. |
| 5,467,911 | A | 11/1995 | Tsuruta et al. |
| 5,476,379 | A | 12/1995 | Disel |
| 5,487,499 | A | 1/1996 | Sorrentino et al. |
| 5,490,683 | A | 2/1996 | Mickel et al. |
| 5,505,737 | A | 4/1996 | Gosselin et al. |
| 5,518,163 | A | 5/1996 | Hooven |
| 5,518,164 | A | 5/1996 | Hooven |
| 5,526,822 | A | 6/1996 | Burbank et al. |
| 5,529,235 | A | 6/1996 | Boiarski et al. |
| 5,535,934 | A | 7/1996 | Boiarski et al. |
| 5,535,937 | A | 7/1996 | Boiarski et al. |
| 5,542,594 | A | 8/1996 | McKean et al. |
| 5,562,239 | A | 10/1996 | Boiarski et al. |
| 5,569,256 | A | 10/1996 | Vaughn et al. |
| 5,601,560 | A | 2/1997 | Del Rio et al. |
| 5,630,818 | A | 5/1997 | Del Rio et al. |
| 5,653,374 | A | 8/1997 | Young et al. |
| 5,667,517 | A | 9/1997 | Hooven |
| 5,704,534 | A | 1/1998 | Huitema et al. |
| 5,713,505 | A | 2/1998 | Huitema |
| 5,741,263 | A | 4/1998 | Umber et al. |
| 5,779,130 | A | 7/1998 | Alesi et al. |
| 5,779,404 | A | 7/1998 | Jore |
| 5,782,397 | A | 7/1998 | Koukline |
| 5,782,836 | A | 7/1998 | Umber et al. |
| 5,820,009 | A | 10/1998 | Melling et al. |
| 5,833,704 | A | 11/1998 | McCombs et al. |
| 5,863,159 | A | 1/1999 | Lasko |
| 5,865,361 | A * | 2/1999 | Milliman ........ A61B 17/07207 227/176.1 |
| 5,888,200 | A | 3/1999 | Walen |
| 5,893,851 | A | 4/1999 | Umber et al. |
| 5,904,687 | A | 5/1999 | Del Rio et al. |
| 5,908,427 | A | 6/1999 | McKean et al. |
| 5,928,238 | A | 7/1999 | Scarborough et al. |
| 5,928,241 | A | 7/1999 | Menut et al. |
| 5,941,891 | A | 8/1999 | Walen |
| 5,954,259 | A | 9/1999 | Viola et al. |
| 5,964,774 | A | 10/1999 | McKean et al. |
| 5,989,257 | A | 11/1999 | Tidwell et al. |
| 5,993,453 | A | 11/1999 | Bullara et al. |
| 5,993,454 | A | 11/1999 | Longo |
| 6,017,354 | A | 1/2000 | Culp et al. |
| 6,033,408 | A | 3/2000 | Gage et al. |
| 6,045,560 | A | 4/2000 | McKean et al. |
| 6,062,575 | A | 5/2000 | Mickel et al. |
| 6,090,123 | A | 7/2000 | Culp et al. |
| 6,129,547 | A | 10/2000 | Cise et al. |
| 6,209,886 | B1 | 4/2001 | Estes et al. |
| 6,264,087 | B1 | 7/2001 | Whitman |
| 6,270,087 | B1 | 8/2001 | Mickel et al. |
| RE37,358 | E | 9/2001 | Del Rio et al. |
| 6,302,311 | B1 | 10/2001 | Adams et al. |
| 6,315,184 | B1 | 11/2001 | Whitman |
| 6,321,855 | B1 | 11/2001 | Barnes |
| 6,329,778 | B1 | 12/2001 | Culp et al. |
| 6,343,731 | B1 | 2/2002 | Adams et al. |
| 6,348,061 | B1 | 2/2002 | Whitman |
| 6,368,324 | B1 | 4/2002 | Dinger et al. |
| 6,434,507 | B1 | 8/2002 | Clayton et al. |
| 6,443,973 | B1 | 9/2002 | Whitman |
| 6,461,372 | B1 | 10/2002 | Jensen et al. |
| 6,488,197 | B1 | 12/2002 | Whitman |
| 6,491,201 | B1 | 12/2002 | Whitman |
| 6,514,001 | B1 * | 2/2003 | Yezersky ............. B60N 2/4838 188/267.1 |
| 6,533,157 | B1 | 3/2003 | Whitman |
| 6,537,280 | B2 | 3/2003 | Dinger et al. |
| 6,610,066 | B2 | 8/2003 | Dinger et al. |
| 6,611,793 | B1 | 8/2003 | Burnside et al. |
| 6,698,643 | B2 | 3/2004 | Whitman |
| 6,699,177 | B1 | 3/2004 | Wang et al. |
| 6,716,233 | B1 | 4/2004 | Whitman |
| 6,792,390 | B1 | 9/2004 | Burnside et al. |
| 6,817,508 | B1 | 11/2004 | Racenet et al. |
| 6,846,308 | B2 | 1/2005 | Whitman et al. |
| 6,846,309 | B2 | 1/2005 | Whitman et al. |
| 6,849,071 | B2 | 2/2005 | Whitman et al. |
| 6,959,852 | B2 | 11/2005 | Shelton, IV et al. |
| 6,964,363 | B2 | 11/2005 | Wales et al. |
| 6,981,628 | B2 | 1/2006 | Wales |
| 6,981,941 | B2 | 1/2006 | Whitman et al. |
| 7,032,798 | B2 | 4/2006 | Whitman et al. |
| 7,055,731 | B2 | 6/2006 | Shelton, IV et al. |
| 7,077,856 | B2 | 7/2006 | Whitman |
| 7,111,769 | B2 | 9/2006 | Wales et al. |
| 7,143,923 | B2 | 12/2006 | Shelton, IV et al. |
| 7,143,925 | B2 | 12/2006 | Shelton, IV et al. |
| 7,143,926 | B2 | 12/2006 | Shelton, IV et al. |
| 7,147,138 | B2 | 12/2006 | Shelton, IV |
| 7,226,460 | B2 * | 6/2007 | Gibson ............. A61B 17/2909 606/180 |
| 7,246,734 | B2 | 7/2007 | Shelton, IV |
| 7,328,828 | B2 | 2/2008 | Ortiz et al. |
| 7,364,061 | B2 | 4/2008 | Swayze et al. |
| 7,380,695 | B2 | 6/2008 | Doll et al. |
| 7,380,696 | B2 | 6/2008 | Shelton, IV et al. |

(56) References Cited

U.S. PATENT DOCUMENTS

| | | |
|---|---|---|
| 7,404,508 B2 | 7/2008 | Smith et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton et al. |
| 7,481,347 B2 | 1/2009 | Roy |
| 7,487,788 B2 * | 2/2009 | Baker .................. A61H 3/02 135/69 |
| 7,487,899 B2 | 2/2009 | Shelton, IV et al. |
| 7,549,564 B2 | 6/2009 | Boudreaux |
| 7,568,603 B2 | 8/2009 | Shelton, IV et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,721,931 B2 | 5/2010 | Shelton, IV et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton et al. |
| 7,799,039 B2 | 9/2010 | Shelton, IV et al. |
| 7,802,712 B2 | 9/2010 | Milliman et al. |
| 7,845,537 B2 | 12/2010 | Shelton, IV et al. |
| 7,905,897 B2 | 3/2011 | Whitman et al. |
| 7,918,230 B2 | 4/2011 | Whitman et al. |
| 7,947,034 B2 | 5/2011 | Whitman |
| 7,951,071 B2 | 5/2011 | Whitman et al. |
| 7,963,433 B2 | 6/2011 | Whitman et al. |
| 7,967,178 B2 | 6/2011 | Scirica et al. |
| 7,992,758 B2 | 8/2011 | Whitman et al. |
| 8,016,855 B2 | 9/2011 | Whitman et al. |
| 8,020,743 B2 | 9/2011 | Shelton, IV |
| 8,157,151 B2 | 4/2012 | Ingmanson et al. |
| 8,186,555 B2 | 5/2012 | Shelton, IV et al. |
| 8,220,367 B2 | 7/2012 | Hsu |
| 8,241,322 B2 | 8/2012 | Whitman et al. |
| 8,292,888 B2 | 10/2012 | Whitman |
| 8,357,144 B2 | 1/2013 | Whitman et al. |
| 8,365,972 B2 | 2/2013 | Aranyi |
| 8,372,057 B2 | 2/2013 | Cude et al. |
| 8,391,957 B2 | 3/2013 | Carlson et al. |
| 8,469,423 B1 * | 6/2013 | Crowley, Jr. ............ B25G 1/04 294/174 |
| 8,490,853 B2 | 7/2013 | Criscuolo et al. |
| 2004/0111012 A1 | 6/2004 | Whitman |
| 2005/0184125 A1 * | 8/2005 | Marczyk ......... A61B 17/07207 227/176.1 |
| 2006/0107982 A1 * | 5/2006 | Tsai ..................... A61H 3/02 135/72 |
| 2006/0142656 A1 | 6/2006 | Malackowski et al. |
| 2006/0226195 A1 * | 10/2006 | Scirica ............ A61B 17/07207 227/175.1 |
| 2007/0029363 A1 | 2/2007 | Popov |
| 2007/0031184 A1 * | 2/2007 | Baxstrom ................ F16B 7/042 403/109.3 |
| 2007/0084897 A1 | 4/2007 | Shelton, IV et al. |
| 2007/0102472 A1 | 5/2007 | Shelton, IV |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175955 A1 | 8/2007 | Shelton, IV et al. |
| 2008/0029570 A1 | 2/2008 | Shelton, IV et al. |
| 2008/0029573 A1 | 2/2008 | Shelton, IV et al. |
| 2008/0029574 A1 | 2/2008 | Shelton, IV et al. |
| 2008/0029575 A1 | 2/2008 | Shelton, IV et al. |
| 2008/0029577 A1 * | 2/2008 | Shelton ................. A61B 17/068 227/176.1 |
| 2008/0058801 A1 | 3/2008 | Taylor et al. |
| 2008/0083807 A1 * | 4/2008 | Beardsley ........ A61B 17/07207 227/175.1 |
| 2008/0083808 A1 * | 4/2008 | Scirica ............ A61B 17/07207 227/175.1 |
| 2008/0083812 A1 * | 4/2008 | Scirica ............ A61B 17/07207 227/176.1 |
| 2008/0109012 A1 | 5/2008 | Falco et al. |
| 2008/0185419 A1 | 8/2008 | Smith et al. |
| 2008/0208195 A1 | 8/2008 | Shores et al. |
| 2008/0251561 A1 | 10/2008 | Eades et al. |
| 2008/0251570 A1 * | 10/2008 | Mastri ............. A61B 17/07207 227/175.1 |
| 2008/0255607 A1 | 10/2008 | Zemlok |
| 2008/0262654 A1 | 10/2008 | Omori et al. |
| 2008/0281336 A1 * | 11/2008 | Zergiebel ............ A61B 17/068 606/142 |
| 2009/0030283 A1 * | 1/2009 | Freystein ........... A61B 1/00128 600/182 |
| 2009/0090763 A1 | 4/2009 | Zemlok et al. |
| 2009/0099876 A1 | 4/2009 | Whitman |
| 2009/0182193 A1 | 7/2009 | Whitman et al. |
| 2009/0206131 A1 * | 8/2009 | Weisenburgh, II ..................... A61B 17/07207 227/175.2 |
| 2009/0209990 A1 | 8/2009 | Yates et al. |
| 2010/0239362 A1 * | 9/2010 | Wareham ................ F16B 7/042 403/109.3 |
| 2010/0292716 A1 * | 11/2010 | Kasvikis ............... A61B 1/0014 606/151 |
| 2010/0324368 A1 * | 12/2010 | Mathieu ................. A61M 39/10 600/131 |
| 2011/0108605 A1 * | 5/2011 | Sapienza .......... A61B 17/07207 227/180.1 |
| 2011/0121049 A1 | 5/2011 | Malinouskas et al. |
| 2011/0218522 A1 | 9/2011 | Whitman |
| 2011/0253765 A1 | 10/2011 | Nicholas et al. |
| 2011/0290855 A1 * | 12/2011 | Moore ................ A61B 17/072 227/180.1 |
| 2012/0076577 A1 * | 3/2012 | Yanagihara ........ A61B 1/00087 403/375 |
| 2012/0104071 A1 * | 5/2012 | Bryant ............. A61B 17/07207 227/175.1 |
| 2013/0098965 A1 * | 4/2013 | Kostrzewski .... A61B 17/07207 227/175.2 |
| 2013/0221063 A1 * | 8/2013 | Aronhalt ............. A61B 17/068 227/176.1 |
| 2013/0245676 A1 * | 9/2013 | Cappola ........... A61B 17/07207 606/213 |
| 2014/0001236 A1 * | 1/2014 | Shelton, IV ...... A61B 17/07207 227/176.1 |
| 2014/0236174 A1 * | 8/2014 | Williams ......... A61B 17/00234 606/130 |
| 2014/0249557 A1 * | 9/2014 | Koch, Jr. ............. A61B 17/072 606/170 |
| 2014/0263568 A1 * | 9/2014 | Williams .......... A61B 17/07207 227/180.1 |
| 2014/0358129 A1 * | 12/2014 | Zergiebel ............... A61B 17/28 606/1 |
| 2015/0327919 A1 * | 11/2015 | Clopp ................ A61B 18/1485 606/41 |

FOREIGN PATENT DOCUMENTS

| | | | |
|---|---|---|---|
| EP | 1736112 | 12/2006 | |
| EP | 1769754 | 4/2007 | |
| EP | 1813203 | 8/2007 | |
| EP | 1943958 | 7/2008 | |
| EP | 1943976 | 7/2008 | |
| EP | 1952769 A2 * | 8/2008 | ........ A61B 17/07207 |
| EP | 2027819 | 2/2009 | |
| EP | 2055243 | 5/2009 | |
| EP | 2098170 | 9/2009 | |
| EP | 2100561 | 9/2009 | |
| WO | WO 00/72760 | 12/2000 | |

(56) References Cited

FOREIGN PATENT DOCUMENTS

| WO | WO 00/72765 | 12/2000 |
|---|---|---|
| WO | WO 03/026511 | 4/2003 |
| WO | WO 03/077769 | 9/2003 |
| WO | WO 2004/107989 | 12/2004 |
| WO | WO 2006/042210 | 4/2006 |
| WO | WO 2007/014355 | 2/2007 |
| WO | WO 2007/026354 | 3/2007 |
| WO | WO 2008/131362 | 10/2008 |
| WO | WO 2008/133956 | 11/2008 |
| WO | WO 2009/039506 | 3/2009 |
| WO | WO 2009/132359 | 10/2009 |

OTHER PUBLICATIONS

International Search Report corresponding to PCT/US2005/027266, completed May 30, 2008 and mailed Jun. 18, 2008; (2 pp.).

Extended European Search Report corresponding to EP 08 25 3184.9, completed Feb. 12, 2009 and mailed Feb. 27, 2009; (3 pp.).
Extended European Search Report corresponding to EP 10 25 0228.3, completed May 20, 2010 and mailed Jun. 1, 2010; (6 pp.).
Extended European Search Report corresponding to EP 10 25 2037.6, completed Mar. 1, 2011 and mailed Mar. 9, 2011; (3 pp.).
Extended European Search Report corresponding to EP 10 25 1968.3, completed on Jul. 4, 2011 and mailed Jul. 14, 2011; (12 pp.).
Extended European Search Report corresponding to EP 11 15 2266.0, completed Jul. 15, 2011 and mailed Jul. 28, 2011; (3 pp.).
Extended European Search Report corresponding to EP 11 25 0462.6, completed Jul. 20, 2011 and mailed Jul. 28, 2011; (6 pp.).
Extended European Search Report corresponding to EP 11 25 0771.0, completed Feb. 7, 2012 and mailed Feb. 17, 2012; (3 pp.).
Extended European Search Report corresponding to EP 06 78 8914.7, completed May 3, 2012 and mailed May 11, 2012; (8 pp.).
Partial European Search Report corresponding to EP 12 18 6177.7, completed Jan. 30, 2013 and mailed Feb. 12, 2013; (6 pp.).

\* cited by examiner

COUPLING MEMBER CONFIGURED FOR USE WITH SURGICAL DEVICES

BACKGROUND

Technical Field

The present disclosure relates to a coupling member for coupling an actuating device to a removable tool assembly. More specifically, the present disclosure relates to a coupling member including a locking assembly for securing a surgical actuating device to a disposable loading unit or reload of a surgical apparatus.

Description of Related Art

Surgical apparatus including a surgical actuating device and a disposable single use or multiple use loading unit or reload are known. Typically, during a surgical procedure, a reload, which may be in the form of a stapler, clip applier or the like, is connected to a surgical actuating device to perform a surgical procedure. After the surgical procedure is completed, the spent reload may be replaced with a fresh reload to facilitate performance of another surgical procedure.

During surgical procedures, it is imperative that the reload be securely fastened to the surgical actuating device in a manner to prevent separation of the reload from the surgical actuating device during actuation of the reload. It is also important that the reload be capable of attachment to and detachment from the surgical actuating device quickly.

SUMMARY

As can be appreciated, an electromechanical surgical device including a tool assembly that is easy to install and configured to lock when the electromechanical surgical device is fired may prove useful in the surgical arena.

Embodiments of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

An aspect of the present disclosure provides a surgical apparatus. The surgical actuating device including a shaft having a distal end supporting a first coupling member. The first coupling member including one or more pairs of aperture. A reload includes a tool assembly. The reload includes a second coupling member including a locking assembly. The second coupling member including a pair of spring pins that are positioned to be received within the at least one pair of apertures. The spring pins being movable from an inward position to a radial outward position. The locking assembly including a lock plate that is moveable from a first position located between the spring pins to prevent movement of the spring pins from the radial outward position to the inward position to a second position spaced from the spring pins. In the radial outward position, the spring pins are received within the apertures of the first coupling member to secure the reload to the surgical actuating member and wherein when the lock plate is in the first position, the reload cannot be separated from the surgical actuating device. The surgical actuating device may be electromechanically actuated.

The second coupling member may include an axle for supporting one or more springs and the pair of spring pins. The spring(s) may be positioned between the pair of spring pins and configured to bias the pair of spring pins to the radial outward position. Each of the spring pins of the second coupling member may include a tapered outer peripheral edge. Contact between the tapered outer edges of the spring pins and an outer edge of the first coupling member cams the spring pins inwardly against the bias of the spring(s).

The lock plate may include one or more hinges that pivotably couple the lock plate to an internal surface of the tool assembly of the reload. The lock plate may include a clevis at a top portion thereof. The clevis may be configured to connect to a proximal end of a plunger of the locking assembly. The plunger may support a spring for biasing the lock plate into engagement with the pair of spring pins when a knife of a cartridge of the tool assembly is fired.

The first coupling member may include two or more pairs of apertures. Each of the pairs of apertures may be configured to engage the pair of spring pins. The two pairs of apertures may be oriented orthogonally in relation to one another.

BRIEF DESCRIPTION OF THE DRAWING

Various embodiments of the present disclosure are described hereinbelow with references to the drawings, wherein.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1:
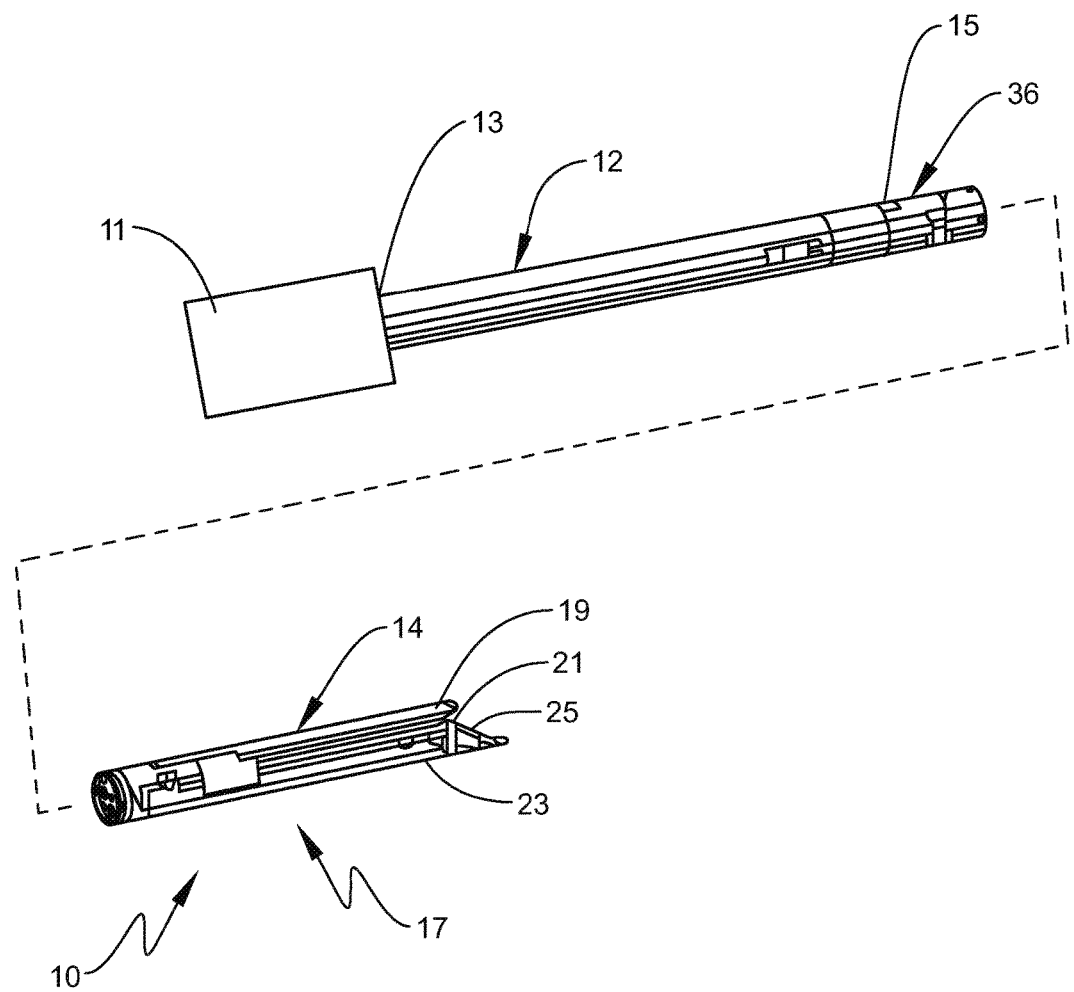
FIG. 1. is a perspective view of a reload, with parts separated, including a shaft including a first coupling member and an end effector member including a tool assembly including a second coupling member according to an embodiment of the instant disclosure.
Figure 2:
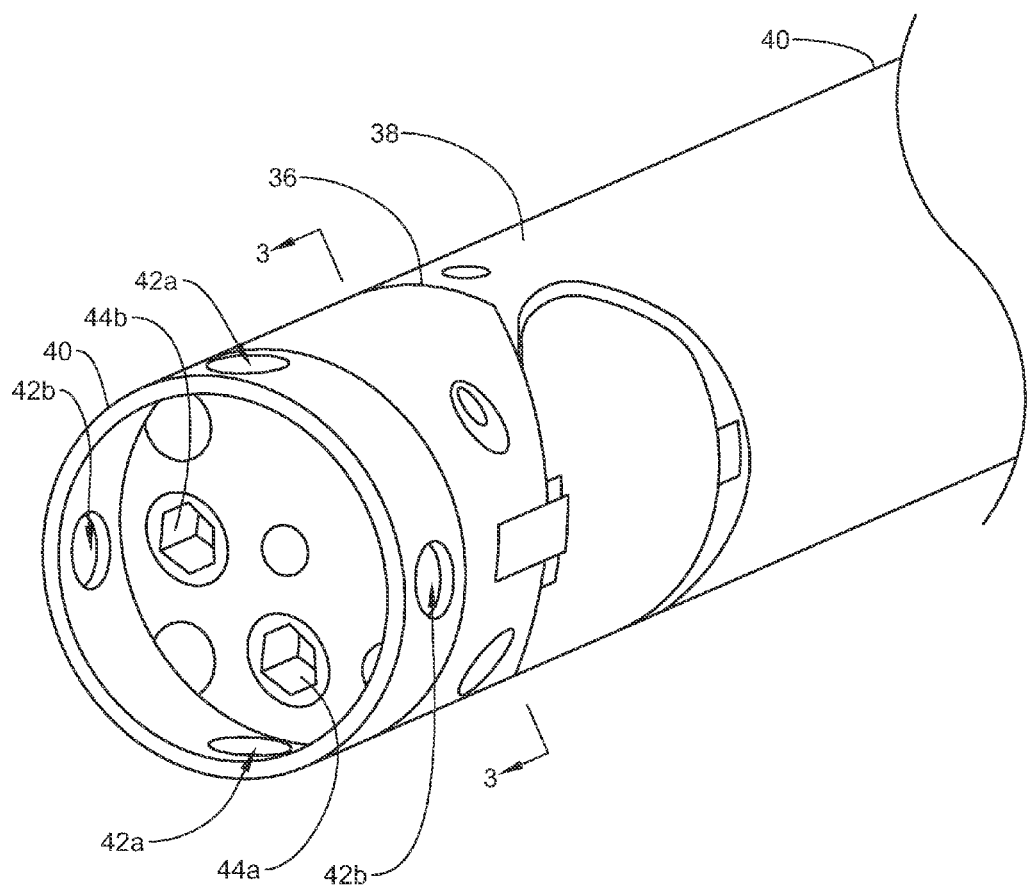
FIG. 2 is a perspective view of the first coupling member disposed at a distal end of the shaft of the reload shown in FIG. 1 according to an embodiment of the instant disclosure.
Figure 3:
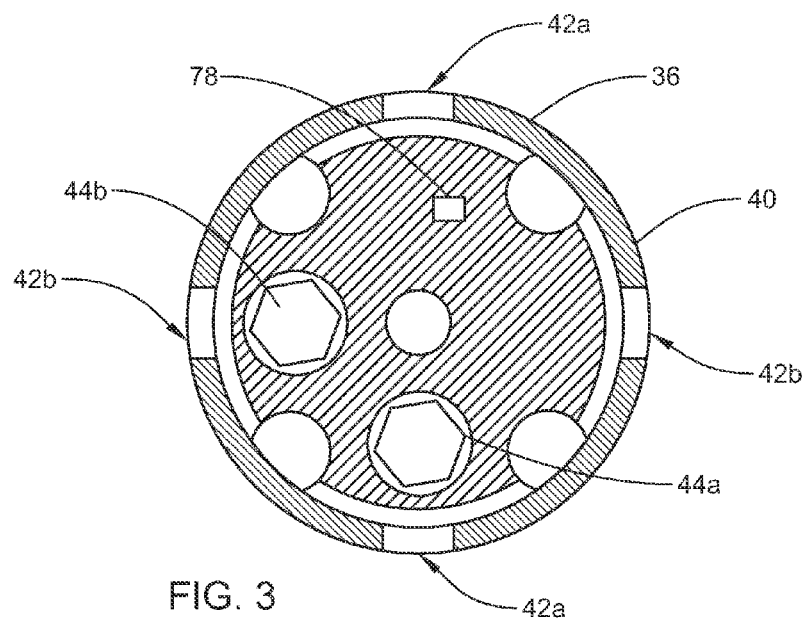
FIG. 3 is a cross sectional view taken along line segment 3-3 in FIG. 2.

Referring initially to FIG. 1, a reload 10 in accordance with the present disclosure is shown. Reload 10 may be configured to be coupled to a variety of different surgical actuating devices, shown schematically as 11 in FIG. 1, including manually operated actuation devices, robotically controlled actuation devices, electromechanical actuation devices, motorized actuation devices, etc. The reload 10 supports an end effector or tool assembly 14 which can be in the form of a stapler, clip applier, grasper or the like.

The surgical actuating device 11 includes a shaft assembly 12 which includes a distal end supporting a first coupling member 36 configured to releasably support the reload 10. In one embodiment, the tool assembly 14 is in the form of a stapler and includes a first jaw member 19 supporting an anvil 21 and a second jaw member 23 supporting a cartridge 25. In any of the embodiments disclosed herein, the cartridge 25 may be removably couplable to the second jaw member 23.

Referring to FIGS. 1-5, the first coupling member 36 is supported at the distal end 15 of the shaft assembly 12 and is configured to be removably coupled to a second coupling member 51 (FIG. 5) of the of the reload 10 to releasably couple the reload 10 to the surgical actuating device 11. The first coupling member 36 includes a collar 40 which includes two pairs of spaced apart apertures 42a, 42b that are oriented orthogonally with respect to one another. The apertures 42a, 42b are arranged to allow a user to couple the reload 10 to the shaft assembly 12 in at least two different positions relative to the distal end 15 of the shaft assembly 12. In embodiments, the apertures 42a, 42b may be tapered, beveled for reasons to be discussed in further detail below.

As noted above, the reload 10 may be configured for use with various surgical instruments. For example, in an embodiment, the reload may be configured for use with a surgical instrument that utilizes electromechanical linear driven actuation. In this particular embodiment, a pair of output drives 44a, 44b may be provided within the coupling member 36 and may be oriented 90 degrees from one another to engage the reload 10 when the reload 10 is coupled to the coupling member 36. The output drives 44a, 44b may be spaced 90 degrees from one another to give a clinician the flexibility to position the rotatably secure the reload 10 to the shaft assembly 12 by rotating the reload 10 in either a clockwise or counter clockwise direction in relation to the shaft assembly 12 as will be discussed in further detail below. In any of the embodiments disclosed herein, the apertures 42a and 42b can be spaced a different angular distance from one another, and the output drives arranged accordingly, so as to provide the surgeon with different orientation of the tool assembly with respect to the shaft of the instrument.

Figure 4:
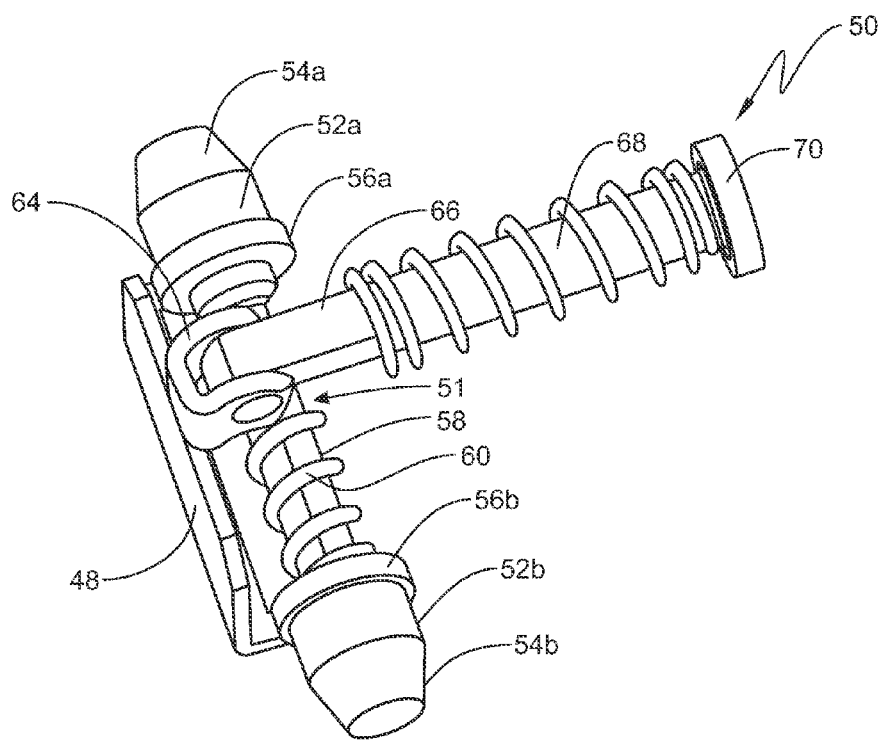
FIG. 4 is a perspective view of a locking assembly and a second coupling member including a pair of spring pins of the end effector shown in FIG. 1.
Figure 5:
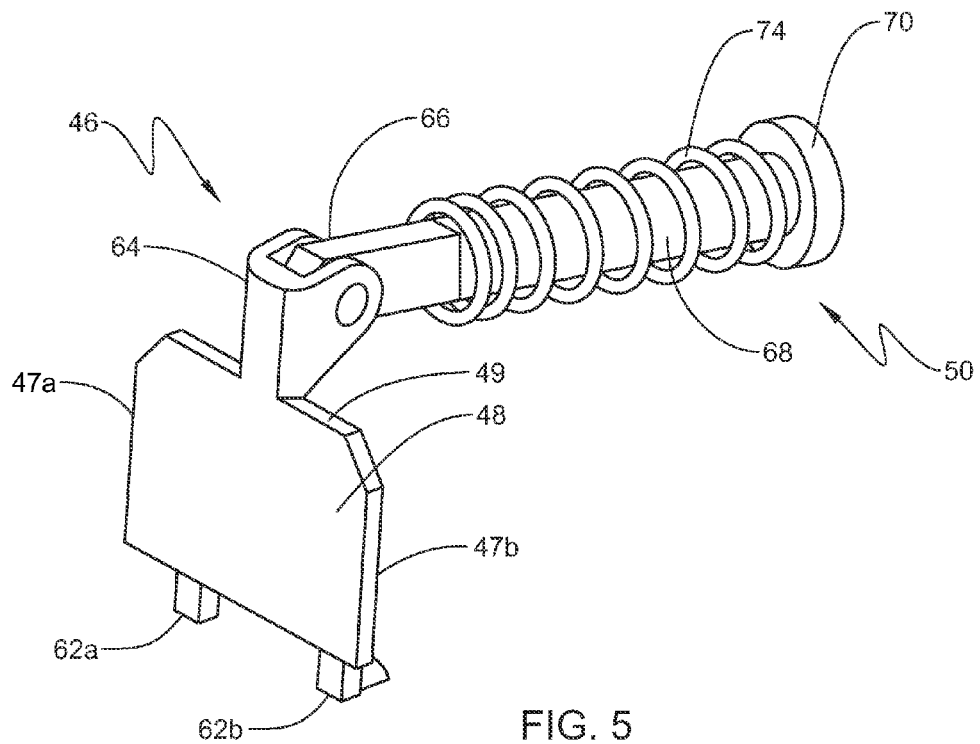
FIG. 5 is a perspective view of a lock plate and plunger of the locking assembly shown in FIG. 4.

Referring to FIGS. 4-5, the reload 10 includes a second coupling member 51. Coupling member 51 includes a pair of spring pins 52a, 52b which are configured to be received within a respective one of the pairs of apertures 42a or 42b defined in the first coupling member 36 for removably coupling the reload 10 to the distal end 15 of the shaft assembly 12. Each of the spring pins 52a, 52b can have a tapered outer peripheral edge 54a, 54b and an annular flange 56a, 56b. The pair of spring pins 52a, 52b is positioned on an axle 58. A biasing member, e.g., a spring 60, is positioned about each axle 58 and includes a first end which abuts a respective annular flange 56a, 56b and a second end which abuts a clevis 64 (FIG. 7) to bias the pair of spring pins 52a, 52b radially outwardly for reception within apertures 42a, 42b of first coupling member 36. The spring pins 52a, 52b are deflectable inwardly against the bias of the spring 60 when the proximal end of reload 10 is inserted into the first coupling member 36. More specifically, when the reload 10 is inserted into the first coupling member 36, the tapered edges 54a, 54b of pins 52a, 52b engage an outer wall of the first coupling member 36 and are cammed inwardly to allow passage of the second coupling member 51 into the first coupling member 36. Prior to positioning the second coupling member 51 within the first coupling member 36, the reload 10 may be rotated in relation to the shaft assembly 12 to align pins 52a, 52b with one of the pair of apertures 42a, 42b defined in the first coupling member 36 such that pins 52a, 52b are received within a respective pair of apertures 42a, 42b. As noted above, the apertures 42a, 42b may tapered, beveled or otherwise configured to guide the spring pins 52a, 52b into one of the corresponding pairs of apertures 42a, 42b on the first coupling member 36.

Figure 6:
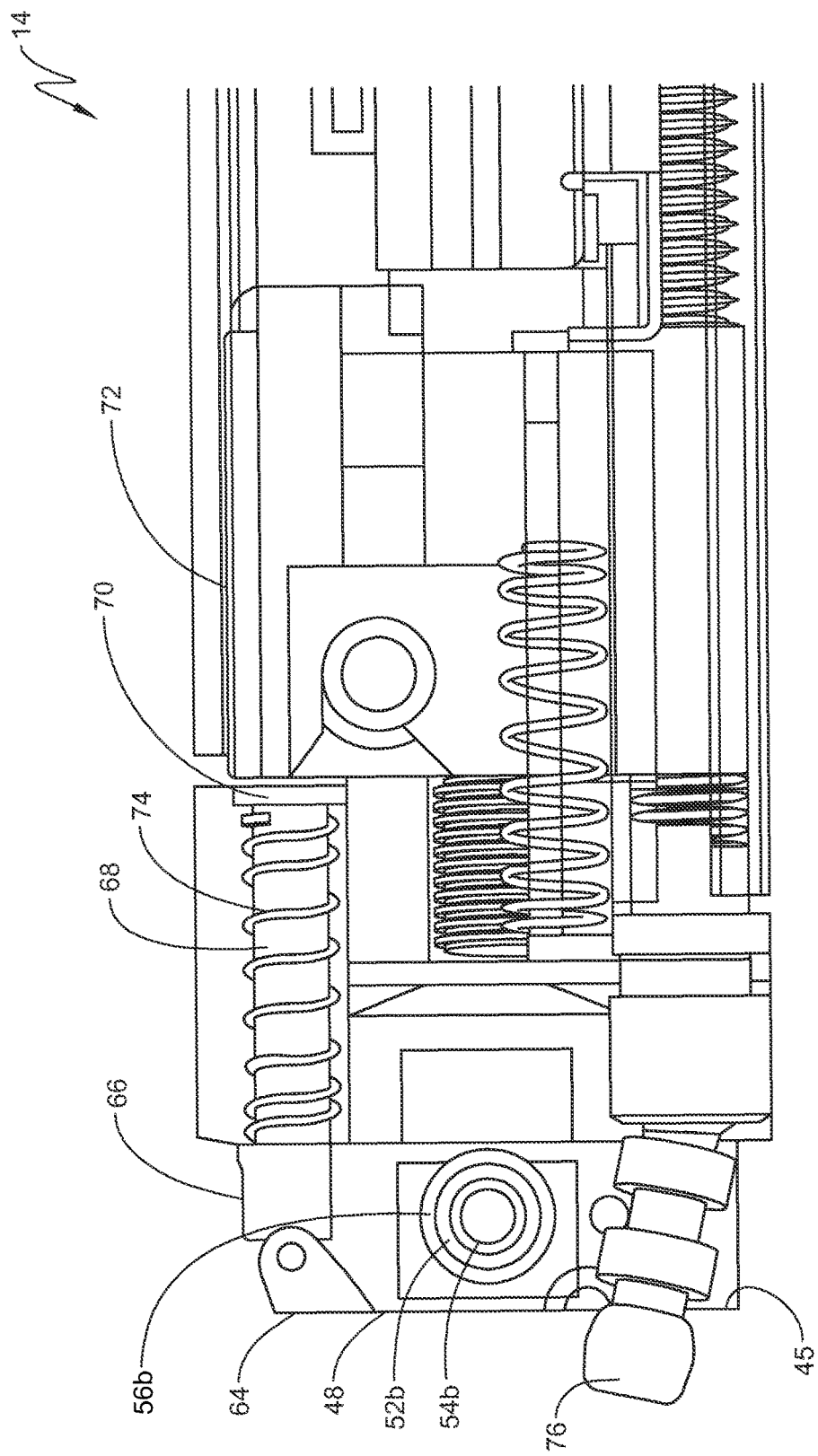
FIG. 6 is a partial, side view of the end effector shown in FIG. 1.

Referring to FIGS. 4-7, the second coupling member 51 also includes a lock assembly which includes a lock plate 48 and a plunger 50. The lock plate 48 includes a pair of left and right hinges 62a, 62b that are pivotably coupled to an internal surface 45 of the tool assembly 14 (as best seen in FIG. 6). Alternatively, a single hinge, living hinge or any structure capable of pivotally supporting the lock plate 48 adjacent the proximal end of the reload 10 may be provided to pivotally support the lock plate 10. In the illustrated embodiment, the lock plate 48 is pivotable about the hinges 62a, 62b from a first unlocked position (FIG. 7) to a second locked position (FIGS. 6 and 8). In the locked position, left and right sidewalls 47a, 47b of the lock plate 48 are positioned between the annular flanges 56a, 56b of spring pins 52a, 52b of the second coupling member 51. In this position, lock plate 48 prevents the spring pins 52a, 52b from moving radially inward and, thus, prevents pins 52a, 52b from exiting the apertures 42a, 42b to prevent separation of the reload 10 from the shaft assembly 12. In the unlocked position, the left and right sidewalls 47a, 47b of the lock plate 48 are not positioned between the annular flanges 56a, 56b of the spring pins 52a, 52b of the second coupling member 51. In this position, the spring pins 52a, 52b are capable of inward movement. A clevis 64 is provided at a top portion 49 of the lock plate 48 and is configured to connect to a proximal end 66 of the plunger 50 to the lock plate 48. The clevis 64 may be connected to the proximal end 66 of the plunger 50 via a pin, detent/indent configuration or other suitable connection method.

The plunger 50 includes an elongated body portion 68 that supports a flange 70 at a distal end thereof. The flange 70 is configured to contact a proximal end of a knife 72 (or clamping member) when the knife 72 is disposed in a proximal most position (see FIG. 7 for example). For a more detailed discussion of the knife 72 and other components of the reload (or loading unit), see U.S. Pat. No. 5,865,361 ('361 patent) which is incorporated herein by reference. A spring 74 is supported about the elongated body portion 68 of the plunger 50 between the flange 70 and an inner wall 70a (FIG. 8) of the reload housing 10a to urge the plunger 68 distally such that flange 70 abuts the knife 72. By biasing plunger 68 distally, lock plate 48 is urged towards the locked position (FIG. 8) between the spring pins 52a, 52b. When the knife 72 is in its proximal-most position, lock plate 48 is prevented from moving to the locked position. As such, when the knife 72 is in its proximal-most position, the reload 10 can be disengaged from the shaft assembly 12 of the surgical actuating device 11.

Figure 7:
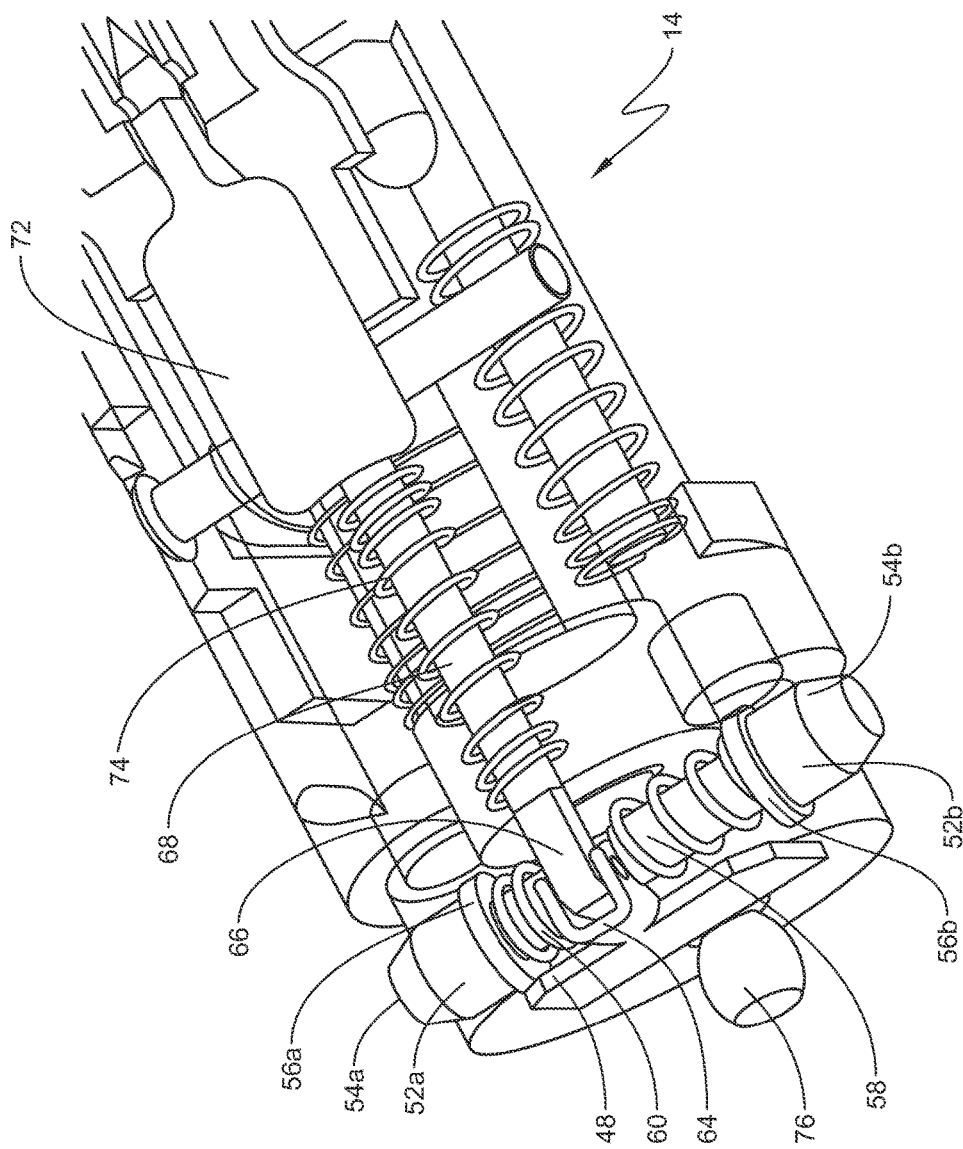
FIG. 7 is a partial, perspective view of the end effector, with an anvil of the tool assembly removed, to illustrate the lock plate and plunger shown in FIG. 5 in an unlocked configuration.
Figure 8:
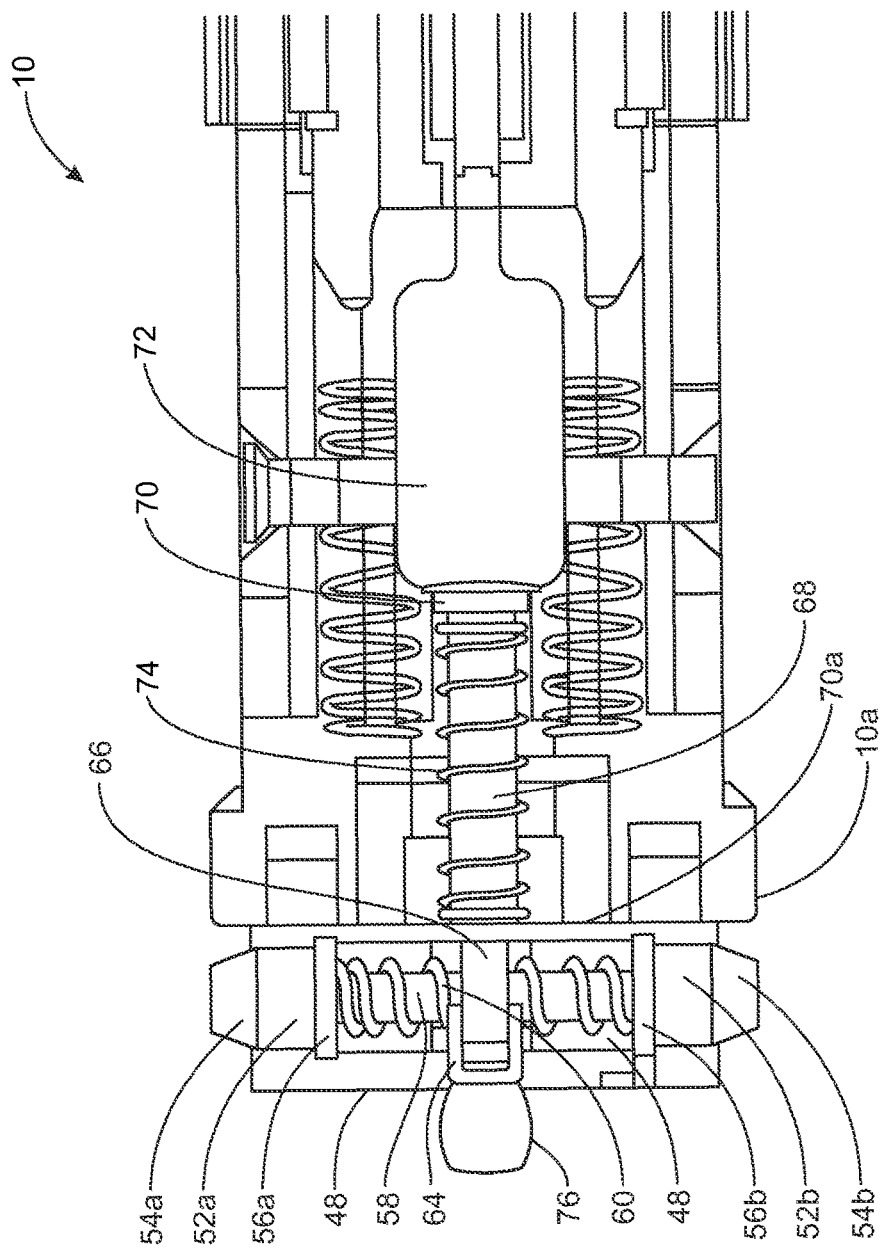
FIG. 8 is a top elevational view of the tool assembly shown in FIG. 7 with an anvil of the tool assembly removed, to illustrate the lock plate and plunger in a locked configuration.

Referring to FIGS. 6-7, as noted above, the surgical actuating device can include an electromechanical linear driven actuation. To this end, the reload 10 can include an input drive 76 at a proximal end of the tool assembly 14 which is configured to selectively engage either one of the output drives 44a, 44b included at the distal end of shaft assembly 12 adjacent the first coupling member 36. In the illustrated embodiment, the input drive 76 includes a hexagonal fitting that is received within a hexagonal recess of the output drives 44a, 44b. The input drive 76 can be connected to either of the output drives 44a, 44b depending on the orientation of the reload 10 in relation to the shaft assembly 12.

Figure 9:
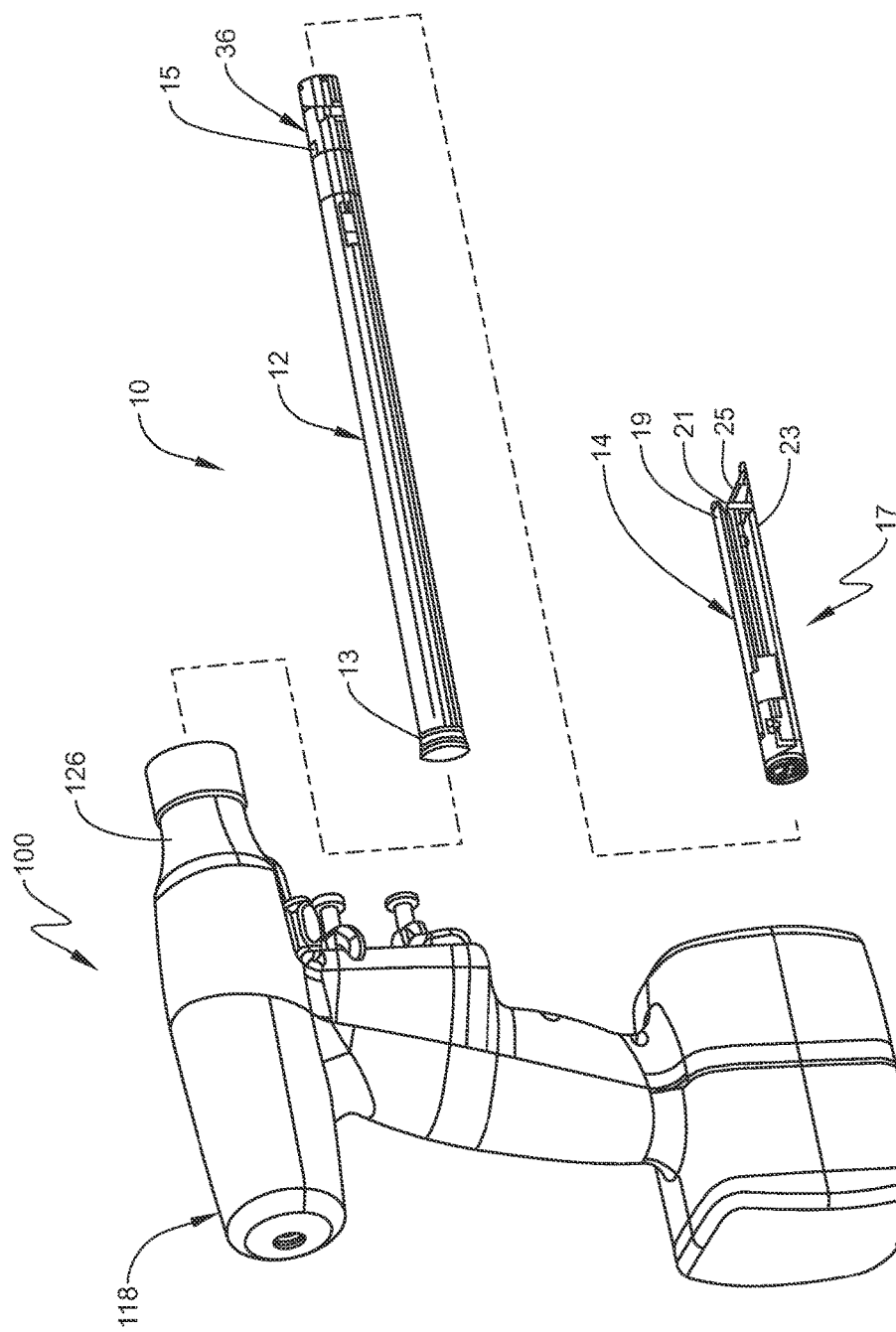
FIG. 9 is a perspective view of a powered surgical instrument configured for use with the reload shown in FIG. 1.

For illustrative purposes, operation of the reload 10 is now described in association with an electromechanical, hand-held surgical stapling apparatus 100 (apparatus 100) shown in FIG. 9. It is noted that the coupling member 51 of reload 10 can be used to couple reload 10 to a variety of different surgical actuating devices 11 as discussed above.

Briefly, apparatus 100 includes a handle 118 that defines a nose or connecting portion 126 configured to releasably engage the proximal end 13 of the shaft assembly 12. Alternatively, the handle 118 and the shaft assembly 12 can be fixedly connected. A drive mechanism (not shown) is configured to drive the output drives 44a, 44b of shaft assembly 12 to actuate the tool assembly 14 to effect movement of anvil 19 and/or to fire the staples and sever tissue. This operation is described in detail in U.S. patent application Ser. Nos. 12/622,827, 13/769,419 which are incorporated herein by reference. In any of the embodiments disclosed herein, the shaft assembly can be removable and replaceable and can correspond to the particular reload being used (such as clip applier, electrosurgical, stapler configurations, etc.) or the shaft assembly can be permanently attached to the handle.

In use, the knife 72 of the cartridge 23 is initially positioned at a proximal end of the cartridge 23. The cartridge 23 can be installed onto a jaw member of the tool assembly 14 (FIG. 7) or, in the alternative, can be fixedly supported on the jaw member of the reload 10. In this position, the plunger 50 of the locking assembly 46 is biased proximally, which, in turn, maintains the lock plate 48 in the unlocked configuration, i.e., the lock plate 48 is positioned proximally of annular flanges 56a, 56b of the spring pins 52a, 52b such that inward movement of the spring pins 52a, 52b is permitted. In this configuration, a proximal end of the tool assembly 14 can be inserted into the first coupling member 36 so that the spring pins 52a, 52b of the second coupling member 51 are received within the pair of apertures 42a, 42b on the first coupling member 36. As can be appreciated, engagement of the tapered peripheral edges 54a, 54b of the spring pins 52a, 52b with the outer edge of the first coupling member 36 cams the spring pins 52a, 52b inwardly against the bias of the spring 60. This allows the first coupling member 36 to move into the second coupling member 51 to move the spring pins 52a, 52b of the second coupling member 51 into the apertures 42a, 42b of the first coupling member 36 to secure the reload 10 to the shaft assembly 12.

When the apparatus 100 is fired to staple tissue, the knife 72 moves out of engagement with the flange 70. When this occurs, the spring 74 urges the plunger 50 distally such that the lock plate 48 of the locking assembly 46 pivots about the hinges 62a, 62b and moves between the inside flange portions 56a, 56b of the spring pins 52a, 52b (FIGS. 6 and 8). In this configuration, the spring pins 52a, 52b are prevented from inward movement. Thus, spring pins 52a, 52b cannot be removed from apertures 42a, 42b and reload 10 cannot be disengaged from the shaft assembly 12.

Thereafter, the knife 72 may be returned to the proximal most position, which, in turn, moves the lock plate 48 proximally from between the spring pins 52a, 52b and out of the locked configuration. In this position, a user can remove the tool assembly 17 from the first coupling member. As noted above, the tapered peripheral edges 54a, 54b of the spring pins 52a, 52b facilitate biasing the spring pins 52a, 52b inwardly against the bias of the spring 60 as the spring pins 52a, 52b are moved into and out of engagement with the apertures 42a, 42b, which, in turn, allows the spring pins 52a, 52b to slide out of engagement with the apertures 42a, 42b with a simple axial motion.

The unique configuration of the locking assembly 46 and spring pins 52a, 52b overcome the aforementioned drawbacks, typically, associated with conventional staplers that are configured for use with removably couplable tool assemblies. That is, the tool assembly 14 is maintained in a locked configuration on at the distal end 15 of the shaft assembly 12 when the apparatus 100 is fired, and the tool assembly 14 can be installed to the first coupling member 36 with a simple straight push/pull motion.

From the foregoing and with reference to the various figure drawings, those skilled in the art will appreciate that certain modifications can also be made to the present disclosure without departing from the scope of the same. For example, one or more sensors 78 (FIG. 4) may be provided in and/or on the first coupling member 36 to detect when the tool assembly 14 is coupled to the first coupling member 36. In this embodiment, the sensor 78 may communicate with one or more components associated with any of the aforementioned surgical devices.

Moreover, the first coupling member 36 of the reload 10 may be modified to receive different linear drive mechanisms. For example, in an embodiment, the reload 19 may be configured to connect to a manually actuatable surgical stapling device that utilizes a drive beam configured to translate within a staple cartridge to fire a sled of the staple cartridge. In this embodiment, for example, the first coupling member 36 may include an aperture, slot or channel configured to receive the drive beam therethrough when the manually actuatable surgical stapling device is fired.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical apparatus comprising:
   a surgical actuating device including a shaft having a distal end supporting a first coupling member, the first coupling member including at least one pair of apertures; and
   a reload including a tool assembly, the reload including a second coupling member including a locking assembly, the second coupling member including a pair of spring pins that are positioned to be received within the at least one pair of apertures, the spring pins being movable from an inward position to a radial outward position, the locking assembly including a lock plate that is moveable from a first position located between the spring pins to prevent movement of the spring pins from the radial outward position to the inward position to a second position spaced from the spring pins, wherein in the radial outward position the spring pins are received within the apertures of the first coupling member to secure the reload to the surgical actuating member and wherein when the lock plate is in the first position, the reload cannot be separated from the surgical actuating device.

2. The surgical apparatus according to claim 1, wherein the second coupling member includes an axle for supporting at least one spring and the pair of spring pins, the at least one spring positioned between the pair of spring pins and configured to bias the pair of spring pins to the radial outward position.

3. The surgical apparatus according to claim 1, wherein each of the spring pins of the second coupling member includes a tapered outer peripheral edge, wherein contact between the tapered outer edges of the spring pins and an outer edge of the first coupling member cams the spring pins inwardly against the bias of the at least one spring.

4. The surgical apparatus according to claim 1, wherein the lock plate includes a clevis at a top portion thereof.

5. The surgical apparatus according to claim 4, wherein the clevis is configured to connect to a proximal end of a plunger of the locking assembly.

6. The surgical apparatus according to claim 1, wherein the first coupling member includes at least two pairs of apertures, each of the pairs of apertures configured to engage the pair of spring pins.

7. The surgical apparatus according to claim 6, wherein the at least two pairs of apertures are oriented orthogonally in relation to one another.

8. The surgical apparatus according to claim 1, wherein the surgical actuating device is electromechanically actuated.

9. A surgical apparatus comprising:
a surgical actuating device including a shaft having a distal end supporting a first coupling member, the first coupling member including at least one pair of apertures; and
a reload including a tool assembly, the reload including a second coupling member including a locking assembly, the second coupling member including a pair of spring pins that are positioned to be received within the at least one pair of apertures, the spring pins being movable from an inward position to a radial outward position, the locking assembly including a lock plate that is moveable from a first position located between the spring pins to prevent movement of the spring pins from the radial outward position to the inward position to a second position spaced from the spring pins, wherein in the radial outward position the spring pins are received within the apertures of the first coupling member to secure the reload to the surgical actuating member and wherein when the lock plate is in the first position, the reload cannot be separated from the surgical actuating device, wherein the lock plate includes at least one hinge that pivotably couples the lock plate to an internal surface of the tool assembly of the reload.

10. A surgical apparatus comprising:
a surgical actuating device including a shaft having a distal end supporting a first coupling member, the first coupling member including at least one pair of apertures; and
a reload including a tool assembly, the reload including a second coupling member including a locking assembly, the second coupling member including a pair of spring pins that are positioned to be received within the at least one pair of apertures, the spring pins being movable from an inward position to a radial outward position, the locking assembly including a lock plate that is moveable from a first position located between the spring pins to prevent movement of the spring pins from the radial outward position to the inward position to a second position spaced from the spring pins, wherein in the radial outward position the spring pins are received within the apertures of the first coupling member to secure the reload to the surgical actuating member and wherein when the lock plate is in the first position, the reload cannot be separated from the surgical actuating device, wherein the lock plate includes a clevis at a top portion thereof, the clevis being configured to connect to a proximal end of a plunger of the locking assembly, and wherein the plunger supports a spring for biasing the lock plate into engagement with the pair of spring pins when a knife of a cartridge of the tool assembly is fired.

* * * * *